United States Patent
Hollis et al.

(10) Patent No.: US 9,254,130 B2
(45) Date of Patent: Feb. 9, 2016

(54) BLADE ANCHOR SYSTEMS FOR BONE FUSION

(71) Applicant: Hyun Bae, Santa Monica, CA (US)

(72) Inventors: M. Chad Hollis, Collierville, TN (US); James Brownhill, Orlando, FL (US)

(73) Assignee: Hyun Bae, Santa Monica, CA (US)

( * ) Notice: Subject to any disclaimer, the term of this patent is extended or adjusted under 35 U.S.C. 154(b) by 178 days.

(21) Appl. No.: 13/666,787

(22) Filed: Nov. 1, 2012

(65) Prior Publication Data

US 2013/0123863 A1    May 16, 2013

Related U.S. Application Data

(60) Provisional application No. 61/554,386, filed on Nov. 1, 2011.

(51) Int. Cl.

| | |
|---|---|
| A61B 17/04 | (2006.01) |
| A61B 17/84 | (2006.01) |
| A61F 2/08 | (2006.01) |
| A61B 17/064 | (2006.01) |
| A61B 17/68 | (2006.01) |
| A61F 2/42 | (2006.01) |

(52) U.S. Cl.
CPC ............ *A61B 17/0642* (2013.01); *A61B 17/68* (2013.01); *A61B 2017/0641* (2013.01); *A61F 2/4261* (2013.01); *A61F 2002/4271* (2013.01)

(58) Field of Classification Search
USPC ............................. 606/328; 623/17.11–17.16
See application file for complete search history.

(56) References Cited

U.S. PATENT DOCUMENTS

| | | |
|---|---|---|
| 3,486,505 A | 12/1969 | Morrison |
| 3,641,590 A | 2/1972 | Michele |
| 3,650,309 A | 3/1972 | Neuschotz |
| 3,842,825 A | 10/1974 | Wagner |
| 3,848,276 A | 11/1974 | Martinez |
| 3,882,917 A | 5/1975 | Orlomoski |
| 3,896,504 A | 7/1975 | Fischer |
| 3,907,017 A | 9/1975 | Stanwick |
| 3,927,503 A | 12/1975 | Wilson |
| 4,011,602 A | 3/1977 | Rybicki |
| 4,047,524 A | 9/1977 | Hall |
| 4,260,005 A | 4/1981 | Stencel |
| 4,349,955 A | 9/1982 | Keen |
| 4,355,429 A | 10/1982 | Mittelmeier |
| 4,484,570 A | 11/1984 | Sutter |
| 4,501,269 A | 2/1985 | Bagby |
| 4,611,581 A | 9/1986 | Steffee |
| 4,642,869 A | 2/1987 | Muller |
| 4,681,589 A | 7/1987 | Tronzo |
| 4,716,893 A | 1/1988 | Fischer |

(Continued)

FOREIGN PATENT DOCUMENTS

| | | |
|---|---|---|
| EP | 179695 A1 | 4/1986 |
| EP | 1327423 | 7/2003 |

(Continued)

*Primary Examiner* — Sameh Boles
(74) *Attorney, Agent, or Firm* — Maywood IP Law; G. Jo Hays; David W. Meibos

(57) ABSTRACT

Fusion devices include blade anchors. The blade anchors may slidingly penetrate a bone or bone fragment, and may induce compression of one bone to another or one fragment to another. The fusion devices may also include a body to which the blade anchors connect.

11 Claims, 9 Drawing Sheets

(56) References Cited

U.S. PATENT DOCUMENTS

| | | |
|---|---|---|
| 4,743,256 A | 5/1988 | Brantigan |
| 4,743,262 A | 5/1988 | Tronzo |
| 4,764,067 A | 8/1988 | Kawashima |
| 4,820,305 A | 4/1989 | Harms |
| 4,834,757 A | 5/1989 | Brantigan |
| 4,838,891 A | 6/1989 | Branemark |
| 4,865,607 A | 9/1989 | Witzel |
| 4,874,389 A | 10/1989 | Downey |
| 4,930,962 A | 6/1990 | Reynolds |
| 4,946,378 A | 8/1990 | Hirayama |
| 4,957,496 A | 9/1990 | Schmidt |
| 5,002,576 A | 3/1991 | Fuhrmann |
| 5,019,103 A | 5/1991 | Van Zile |
| 5,074,880 A | 12/1991 | Mansat |
| 5,147,361 A | 9/1992 | Ojima |
| 5,163,960 A | 11/1992 | Bonutti |
| 5,192,324 A | 3/1993 | Kenna |
| 5,192,327 A | 3/1993 | Brantigan |
| 5,306,309 A | 4/1994 | Wagner |
| 5,314,477 A | 5/1994 | Marnay |
| 5,431,658 A | 7/1995 | Moskovich |
| 5,443,515 A | 8/1995 | Cohen |
| 5,449,359 A | 9/1995 | Groiso |
| D364,462 S | 11/1995 | Michelson |
| 5,507,816 A | 4/1996 | Bullivant |
| 5,514,180 A | 5/1996 | Heggeness |
| D378,409 S | 3/1997 | Michelson |
| 5,609,635 A | 3/1997 | Michelson |
| 5,658,337 A | 8/1997 | Kohrs |
| 5,660,188 A | 8/1997 | Groiso |
| 5,683,394 A | 11/1997 | Rinner |
| 5,702,449 A | 12/1997 | McKay |
| 5,709,683 A | 1/1998 | Bagby |
| 5,713,899 A | 2/1998 | Marnay |
| 5,769,852 A | 6/1998 | Branemark |
| 5,772,661 A | 6/1998 | Michelson |
| 5,776,199 A | 7/1998 | Michelson |
| 5,776,202 A | 7/1998 | Copf |
| 5,788,701 A | 8/1998 | McCue |
| 5,800,550 A | 9/1998 | Sertich |
| 5,853,414 A | 12/1998 | Groiso |
| 5,860,973 A | 1/1999 | Michelson |
| 5,885,287 A | 3/1999 | Bagby |
| 5,893,889 A | 4/1999 | Harrington |
| 5,893,890 A | 4/1999 | Pisharodi |
| 5,947,999 A | 9/1999 | Groiso |
| 5,993,476 A | 11/1999 | Groiso |
| 6,039,762 A | 3/2000 | McKay |
| 6,063,121 A | 5/2000 | Xavier |
| 6,080,155 A | 6/2000 | Michelson |
| 6,096,080 A | 8/2000 | Nicholson |
| 6,102,949 A | 8/2000 | Biedermann |
| 6,113,638 A | 9/2000 | Williams |
| 6,120,503 A | 9/2000 | Michelson |
| 6,136,001 A | 10/2000 | Michelson |
| 6,159,214 A | 12/2000 | Michelson |
| 6,224,607 B1 | 5/2001 | Michelson |
| 6,235,059 B1 | 5/2001 | Benezech |
| 6,241,769 B1 | 6/2001 | Nicholson |
| 6,241,770 B1 | 6/2001 | Michelson |
| 6,270,498 B1 | 8/2001 | Michelson |
| 6,302,914 B1 | 10/2001 | Michelson |
| 6,309,421 B1 | 10/2001 | Pisharodi |
| 6,325,805 B1 | 12/2001 | Ogilvie |
| 6,336,928 B1 | 1/2002 | Guerin |
| 6,364,880 B1 | 4/2002 | Michelson |
| 6,402,785 B1 | 6/2002 | Zdeblick |
| 6,413,278 B1 | 7/2002 | Marchosky |
| 6,432,107 B1 | 8/2002 | Ferree |
| 6,436,098 B1 | 8/2002 | Michelson |
| 6,447,524 B1 | 9/2002 | Knodel |
| 6,447,544 B1 | 9/2002 | Michelson |
| 6,447,546 B1 | 9/2002 | Bramlet |
| 6,458,159 B1 | 10/2002 | Thalgott |
| 6,478,800 B1 | 11/2002 | Fraser |
| 6,485,517 B1 | 11/2002 | Michelson |
| 6,506,216 B1 | 1/2003 | McCue |
| 6,537,320 B1 | 3/2003 | Michelson |
| 6,558,423 B1 | 5/2003 | Michelson |
| 6,558,424 B2 | 5/2003 | Thalgott |
| 6,582,468 B1 | 6/2003 | Gauchet |
| 6,599,294 B2 | 7/2003 | Fuss |
| 6,610,093 B1 | 8/2003 | Pisharodi |
| 6,620,198 B2 | 9/2003 | Burstein |
| 6,652,533 B2 | 11/2003 | O'Neil |
| 6,679,887 B2 | 1/2004 | Nicholson |
| 6,716,245 B2 | 4/2004 | Pasquet |
| 6,726,720 B2 | 4/2004 | Ross |
| 6,740,118 B2 | 5/2004 | Eisermann |
| 6,743,256 B2 | 6/2004 | Mason |
| 6,746,450 B1 | 6/2004 | Wall |
| 6,755,841 B2 | 6/2004 | Fraser |
| 6,767,367 B1 | 7/2004 | Michelson |
| 6,770,074 B2 | 8/2004 | Michelson |
| 6,770,096 B2 | 8/2004 | Bolger |
| 6,773,437 B2 | 8/2004 | Ogilvie |
| 6,800,093 B2 | 10/2004 | Nicholson |
| 6,802,863 B2 | 10/2004 | Lawson |
| 6,827,740 B1 | 12/2004 | Michelson |
| 6,835,208 B2 | 12/2004 | Marchosky |
| 6,849,093 B2 | 2/2005 | Michelson |
| 6,875,213 B2 | 4/2005 | Michelson |
| 6,923,810 B1 | 8/2005 | Michelson |
| 6,923,830 B2 | 8/2005 | Michelson |
| 6,926,718 B1 | 8/2005 | Michelson |
| 6,969,390 B2 | 11/2005 | Michelson |
| 6,972,035 B2 | 12/2005 | Michelson |
| 6,981,975 B2 | 1/2006 | Michelson |
| 6,989,031 B2 | 1/2006 | Michelson |
| 7,033,394 B2 | 4/2006 | Michelson |
| 7,041,135 B2 | 5/2006 | Michelson |
| 7,044,972 B2 | 5/2006 | Mathys, Jr. |
| 7,048,766 B2 | 5/2006 | Ferree |
| 7,056,344 B2 | 6/2006 | Huppert |
| 7,056,345 B2 | 6/2006 | Kuslich |
| 7,060,097 B2 | 6/2006 | Fraser |
| 7,066,961 B2 | 6/2006 | Michelson |
| 7,083,623 B2 | 8/2006 | Michelson |
| 7,083,652 B2 | 8/2006 | McCue |
| 7,087,082 B2 | 8/2006 | Paul |
| 7,112,206 B2 | 9/2006 | Michelson |
| 7,115,146 B2 | 10/2006 | Boyer, II |
| 7,118,580 B1 | 10/2006 | Beyersdorff |
| 7,128,761 B2 | 10/2006 | Kuras |
| 7,163,560 B2 | 1/2007 | Mason |
| 7,166,110 B2 | 1/2007 | Yundt |
| 7,166,129 B2 | 1/2007 | Michelson |
| 7,169,182 B2 | 1/2007 | Errico |
| 7,204,852 B2 | 4/2007 | Marnay |
| 7,235,101 B2 | 6/2007 | Berry |
| 7,235,105 B2 | 6/2007 | Jackson |
| 7,255,698 B2 | 8/2007 | Michelson |
| 7,320,707 B2 | 1/2008 | Zucherman |
| 7,326,248 B2 | 2/2008 | Michelson |
| 7,331,995 B2 | 2/2008 | Eisermann |
| 7,357,817 B2 | 4/2008 | D'Alessio, II |
| 7,364,589 B2 | 4/2008 | Eisermann |
| 7,396,365 B2 | 7/2008 | Michelson |
| 7,462,196 B2 | 12/2008 | Fraser |
| 7,481,830 B2 | 1/2009 | Wall |
| 7,491,205 B1 | 2/2009 | Michelson |
| 7,503,933 B2 | 3/2009 | Michelson |
| 7,503,934 B2 | 3/2009 | Eisermann |
| 7,503,935 B2 | 3/2009 | Zucherman |
| D594,986 S | 6/2009 | Miles |
| 7,540,882 B2 | 6/2009 | Michelson |
| 7,556,650 B2 | 7/2009 | Collins |
| 7,572,293 B2 | 8/2009 | Rhodes |
| 7,588,600 B2 | 9/2009 | Benzel |
| 7,594,931 B2 | 9/2009 | Louis |
| 7,611,538 B2 | 11/2009 | Belliard |
| 7,658,766 B2 | 2/2010 | Melkent |
| 7,695,516 B2 | 4/2010 | Zeegers |
| 7,749,271 B2 | 7/2010 | Fischer |

(56) References Cited

U.S. PATENT DOCUMENTS

| | | |
|---|---|---|
| 7,763,076 B2 | 7/2010 | Navarro |
| 7,780,676 B2 | 8/2010 | Lakin |
| 7,837,732 B2 | 11/2010 | Zucherman |
| 7,896,919 B2 | 3/2011 | Belliard |
| 7,909,871 B2 | 3/2011 | Abdou |
| 7,918,891 B1 | 4/2011 | Curran |
| 8,021,403 B2 | 9/2011 | Wall |
| 8,034,076 B2 | 10/2011 | Criscuolo |
| 8,100,974 B2 | 1/2012 | Duggal |
| 8,105,389 B2 | 1/2012 | Berelsman |
| 8,123,757 B2 | 2/2012 | Zalenski |
| 8,133,283 B2 | 3/2012 | Wilson |
| 8,157,865 B2 | 4/2012 | Hochschuler |
| 8,491,598 B2 | 7/2013 | Crook |
| 8,500,747 B2 | 8/2013 | DeRidder |
| 2001/0000532 A1 | 4/2001 | Michelson |
| 2001/0010001 A1 | 7/2001 | Michelson |
| 2001/0010002 A1 | 7/2001 | Michelson |
| 2001/0010020 A1 | 7/2001 | Michelson |
| 2001/0037154 A1 | 11/2001 | Martin |
| 2001/0047207 A1 | 11/2001 | Michelson |
| 2001/0047208 A1 | 11/2001 | Michelson |
| 2002/0004683 A1 | 1/2002 | Michelson |
| 2002/0013624 A1 | 1/2002 | Michelson |
| 2002/0035400 A1 | 3/2002 | Bryan |
| 2002/0049447 A1 | 4/2002 | Li |
| 2002/0091390 A1 | 7/2002 | Michelson |
| 2002/0091392 A1 | 7/2002 | Michelson |
| 2002/0095155 A1 | 7/2002 | Michelson |
| 2002/0099376 A1 | 7/2002 | Michelson |
| 2002/0099378 A1 | 7/2002 | Michelson |
| 2002/0116065 A1 | 8/2002 | Jackson |
| 2002/0116165 A1 | 8/2002 | El-Ghoroury |
| 2002/0147454 A1 | 10/2002 | Neto |
| 2002/0147499 A1 | 10/2002 | Shea |
| 2002/0161443 A1 | 10/2002 | Michelson |
| 2002/0165613 A1 | 11/2002 | Lin |
| 2003/0023307 A1 | 1/2003 | Michelson |
| 2003/0040798 A1 | 2/2003 | Michelson |
| 2003/0045940 A1 | 3/2003 | Eberlein |
| 2003/0060884 A1 | 3/2003 | Fell |
| 2003/0100949 A1 | 5/2003 | Michelson |
| 2003/0120344 A1 | 6/2003 | Michelson |
| 2003/0149483 A1 | 8/2003 | Michelson |
| 2003/0158553 A1 | 8/2003 | Michelson |
| 2003/0195517 A1 | 10/2003 | Michelson |
| 2003/0195632 A1 | 10/2003 | Foley |
| 2004/0030336 A1 | 2/2004 | Khanna |
| 2004/0030339 A1 | 2/2004 | Wack |
| 2004/0034353 A1 | 2/2004 | Michelson |
| 2004/0064185 A1 | 4/2004 | Michelson |
| 2004/0073315 A1 | 4/2004 | Justin |
| 2004/0083005 A1 | 4/2004 | Jacobsson |
| 2004/0117018 A1 | 6/2004 | Michelson |
| 2004/0133203 A1 | 7/2004 | Young |
| 2004/0148028 A1 | 7/2004 | Ferree |
| 2004/0176853 A1 | 9/2004 | Sennett |
| 2004/0193271 A1 | 9/2004 | Fraser |
| 2004/0199254 A1 | 10/2004 | Louis |
| 2004/0210313 A1 | 10/2004 | Michelson |
| 2004/0210314 A1 | 10/2004 | Michelson |
| 2004/0215203 A1 | 10/2004 | Michelson |
| 2004/0220668 A1 | 11/2004 | Eisermann |
| 2004/0220670 A1 | 11/2004 | Eisermann |
| 2004/0225295 A1 | 11/2004 | Zubok |
| 2004/0225365 A1 | 11/2004 | Eisermann |
| 2004/0230308 A1 | 11/2004 | Michelson |
| 2004/0249388 A1 | 12/2004 | Michelson |
| 2004/0254581 A1 | 12/2004 | Leclair |
| 2004/0254644 A1 | 12/2004 | Taylor |
| 2004/0260286 A1 | 12/2004 | Ferree |
| 2005/0004672 A1 | 1/2005 | Pafford |
| 2005/0014919 A1 | 1/2005 | Hatakeyama |
| 2005/0027300 A1 | 2/2005 | Hawkins |
| 2005/0038512 A1 | 2/2005 | Michelson |
| 2005/0038513 A1 | 2/2005 | Michelson |
| 2005/0043802 A1 | 2/2005 | Eisermann |
| 2005/0049600 A1 | 3/2005 | Groiso |
| 2005/0055031 A1 | 3/2005 | Lim |
| 2005/0125065 A1 | 6/2005 | Zucherman |
| 2005/0131545 A1 | 6/2005 | Chervitz |
| 2005/0143747 A1 | 6/2005 | Zubok |
| 2005/0149192 A1 | 7/2005 | Zucherman |
| 2005/0149193 A1 | 7/2005 | Zucherman |
| 2005/0165408 A1 | 7/2005 | Puno |
| 2005/0171606 A1 | 8/2005 | Michelson |
| 2005/0171607 A1 | 8/2005 | Michelson |
| 2005/0177239 A1 | 8/2005 | Steinberg |
| 2005/0187628 A1 | 8/2005 | Michelson |
| 2005/0187629 A1 | 8/2005 | Michelson |
| 2005/0192586 A1 | 9/2005 | Zucherman |
| 2005/0216083 A1 | 9/2005 | Michelson |
| 2005/0216089 A1 | 9/2005 | Michelson |
| 2005/0273108 A1 | 12/2005 | Groiso |
| 2005/0277933 A1 | 12/2005 | Wall |
| 2006/0004453 A1 | 1/2006 | Bartish |
| 2006/0074421 A1 | 4/2006 | Bickley |
| 2006/0079961 A1 | 4/2006 | Michelson |
| 2006/0085071 A1 | 4/2006 | Lechmann |
| 2006/0095136 A1 | 5/2006 | McLuen |
| 2006/0111787 A1 | 5/2006 | Bailie |
| 2006/0116769 A1 | 6/2006 | Marnay |
| 2006/0122702 A1 | 6/2006 | Michelson |
| 2006/0129238 A1 | 6/2006 | Paltzer |
| 2006/0136061 A1 | 6/2006 | Navarro |
| 2006/0136063 A1 | 6/2006 | Zeegers |
| 2006/0142860 A1 | 6/2006 | Navarro |
| 2006/0149377 A1 | 7/2006 | Navarro |
| 2006/0149384 A1 | 7/2006 | Navarro |
| 2006/0167461 A1 | 7/2006 | Hawkins |
| 2006/0178745 A1 | 8/2006 | Bartish |
| 2006/0195097 A1 | 8/2006 | Evans |
| 2006/0241641 A1 | 10/2006 | Albans |
| 2006/0259143 A1 | 11/2006 | Navarro |
| 2006/0259145 A1 | 11/2006 | Navarro |
| 2006/0259146 A1 | 11/2006 | Navarro |
| 2007/0010890 A1 | 1/2007 | Collazo |
| 2007/0050032 A1 | 3/2007 | Gittings |
| 2007/0055376 A1 | 3/2007 | Michelson |
| 2007/0073404 A1 | 3/2007 | Rashbaum |
| 2007/0093839 A1 | 4/2007 | Beckendorf |
| 2007/0106388 A1 | 5/2007 | Michelson |
| 2007/0118132 A1 | 5/2007 | Culbert |
| 2007/0118145 A1 | 5/2007 | Fischer |
| 2007/0123903 A1 | 5/2007 | Raymond |
| 2007/0142922 A1 | 6/2007 | Lewis |
| 2007/0185375 A1 | 8/2007 | Stad |
| 2007/0191850 A1 | 8/2007 | Kim |
| 2007/0233244 A1* | 10/2007 | Lopez et al. ............... 623/17.11 |
| 2007/0239278 A1 | 10/2007 | Heinz |
| 2007/0288005 A1 | 12/2007 | Arnin |
| 2007/0288021 A1 | 12/2007 | Rickels |
| 2007/0299529 A1 | 12/2007 | Rhodes |
| 2008/0015702 A1 | 1/2008 | Lakin |
| 2008/0051901 A1 | 2/2008 | De Villiers |
| 2008/0051902 A1 | 2/2008 | Dwyer |
| 2008/0103598 A1 | 5/2008 | Trudeau |
| 2008/0132949 A1 | 6/2008 | Aferzon |
| 2008/0140208 A1 | 6/2008 | Zucherman |
| 2008/0147203 A1 | 6/2008 | Cronin |
| 2008/0154377 A1 | 6/2008 | Voellmicke |
| 2008/0167721 A1 | 7/2008 | Bao |
| 2008/0177275 A1 | 7/2008 | Wing |
| 2008/0208345 A1 | 8/2008 | Hurlbert |
| 2008/0249575 A1 | 10/2008 | Waugh |
| 2008/0249623 A1 | 10/2008 | Bao |
| 2008/0269764 A1 | 10/2008 | Blain |
| 2008/0275455 A1 | 11/2008 | Berry |
| 2008/0287957 A1 | 11/2008 | Hester |
| 2009/0005784 A1 | 1/2009 | Blain |
| 2009/0005870 A1 | 1/2009 | Hawkins |
| 2009/0048604 A1 | 2/2009 | Milz |
| 2009/0062921 A1 | 3/2009 | Michelson |
| 2009/0088849 A1 | 4/2009 | Armstrong |

(56) References Cited

U.S. PATENT DOCUMENTS

| | | |
|---|---|---|
| 2009/0099601 A1 | 4/2009 | Aferzon |
| 2009/0099602 A1 | 4/2009 | Aflatoon |
| 2009/0164020 A1 | 6/2009 | Janowski |
| 2009/0209967 A1 | 8/2009 | Evans |
| 2009/0240333 A1 | 9/2009 | Trudeau |
| 2010/0004747 A1 | 1/2010 | Lin |
| 2010/0069958 A1* | 3/2010 | Sullivan et al. ............... 606/232 |
| 2010/0185287 A1 | 7/2010 | Allard |
| 2010/0185292 A1 | 7/2010 | Hochschuler |
| 2010/0201739 A1 | 8/2010 | Yamaguchi |
| 2010/0204737 A1 | 8/2010 | Bae |
| 2010/0204739 A1 | 8/2010 | Bae |
| 2011/0022176 A1 | 1/2011 | Zucherman |
| 2011/0098819 A1 | 4/2011 | Eisermann |
| 2011/0160866 A1 | 6/2011 | Laurence |
| 2011/0166608 A1 | 7/2011 | Duggal |
| 2012/0215315 A1 | 8/2012 | Hochschuler |
| 2012/0253406 A1 | 10/2012 | Bae |
| 2012/0265259 A1 | 10/2012 | LaPosta |
| 2013/0013006 A1 | 1/2013 | Rashbaum |

FOREIGN PATENT DOCUMENTS

| | | |
|---|---|---|
| EP | 1790298 | 5/2007 |
| EP | 1827318 | 9/2007 |
| EP | 1872746 | 1/2008 |
| EP | 1897517 | 3/2008 |
| EP | 1983941 | 10/2008 |
| WO | WO9322990 | 11/1993 |
| WO | WO00025707 | 5/2000 |
| WO | WO00064360 | 11/2000 |
| WO | WO0103570 | 1/2001 |
| WO | WO0203885 | 1/2002 |
| WO | WO00203895 | 1/2002 |
| WO | WO0258593 | 8/2002 |
| WO | WO0305939 | 1/2003 |
| WO | WO03039400 | 5/2003 |
| WO | WO03053290 A1 | 7/2003 |
| WO | WO0365930 | 8/2003 |
| WO | WO0392507 | 11/2003 |
| WO | WO2004071359 A2 | 8/2004 |
| WO | WO2004080355 | 9/2004 |
| WO | WO2004089240 | 10/2004 |
| WO | WO2004108015 | 12/2004 |
| WO | WO2005051243 A2 | 6/2005 |
| WO | WO2005074841 A1 | 8/2005 |
| WO | WO2006051547 A2 | 5/2006 |
| WO | WO2006074414 A2 | 7/2006 |
| WO | WO2006086494 A2 | 8/2006 |
| WO | WO2006120505 | 11/2006 |
| WO | WO2007028098 | 3/2007 |
| WO | WO2007034310 | 3/2007 |
| WO | WO2007087366 A2 | 8/2007 |
| WO | WO2008014258 A2 | 1/2008 |
| WO | WO2008014453 | 1/2008 |
| WO | WO2008021955 A2 | 2/2008 |
| WO | WO2008034140 | 3/2008 |
| WO | WO2008128367 A1 | 10/2008 |
| WO | WO2009070721 | 6/2009 |
| WO | WO2010039026 | 4/2010 |
| WO | WO2010121002 | 10/2010 |
| WO | WO2011044879 | 4/2011 |
| WO | WO2011090508 A1 | 7/2011 |

* cited by examiner

BLADE ANCHOR SYSTEMS FOR BONE FUSION

CROSS-REFERENCE TO RELATED APPLICATIONS

This application is a non-provisional of:

U.S. Provisional Patent Application No. 61/554,386, filed Nov. 1, 2011 and entitled BLADE ANCHOR SYSTEMS FOR BONE FUSION.

The above-identified document is herein incorporated by reference in its entirety.

BACKGROUND OF THE DISCLOSURE

The present disclosure relates to embodiments of blade anchor fusion devices that may be used to fuse the carpal bones, such as the hamate, lunate, capitate and triquetrum. It will be appreciated that any of the disclosed embodiments may have application outside of carpal bone fusion applications, and may be used to provide compression across a fusion or fracture line in any application where a typical fusion device or bone staple may be used. It will also be appreciated that any of the below named embodiments can be mixed and matched to form alternate embodiments.

An example of the present technology is concerned with fusion of the carpal bones by blade anchors that extend outward from a central body. The blade anchors may be secured to the body by a proximal threaded cap.

Those of skill in the art will recognize that the following description is merely illustrative of the principles of the disclosure, which may be applied in various ways to provide many different alternative embodiments and may be applicable outside the fields of surgery or medical devices. While the present disclosure is made in the context of fusing the carpal bones in the wrist for the purposes of illustrating the concepts of the design, it is contemplated that the present design and/or variations thereof may be suited to other uses, such as fusing the tarsal bones of the foot, or other joints in the human body, or to stabilize bone fractures, etc. Moreover, the implants, instrumentation and methods set forth herein may be used in open, percutaneous, and/or minimally invasive procedures.

All changes which come within the meaning and range of equivalency of the claims are to be embraced within their scope.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

SUMMARY

In an aspect of the technology, a fusion device includes a body with a first end, a second end opposite the first end, and a plurality of undercut slots extending between the first and second ends; and at least one anchor with a protrusion, an arm, and a blade, the protrusion engaging a correspondingly shaped one of the plurality of undercut slots, the arm extending outward from the body and terminating in the blade, the blade extending transverse to the arm.

In an embodiment, the first and second ends are planar, and the body includes a cylinder extending between the first and second ends.

In another embodiment, the protrusion is axially movable along the correspondingly shaped one of the plurality of undercut slots.

In yet another embodiment, a second anchor includes a second protrusion, and the second anchor engages a second correspondingly shaped one of the plurality of undercut slots.

In yet another embodiment, the second anchor includes a second arm, wherein the second arm is longer than the first arm.

In yet another embodiment, the device includes a cap threadedly connected to the first end of the body.

In yet another embodiment, the anchor includes a tapered portion adjacent to the second end of the body.

In another aspect of the technology, a fusion device includes a first component with a first body, a first arm, a first blade, and a protruding connecting feature, wherein the first arm extends outward from the first body and terminates in the first blade, wherein the first blade extends transverse to the first arm, wherein the protruding connecting feature protrudes from the first body; and a second component including a second body, a second arm, a second blade, and a receptacle, wherein the second arm extends outward from the second body and terminates in the second blade, wherein the second blade extends transverse to the second arm, wherein the receptacle is recessed within the second body; wherein the first and second components are coupled together, the protruding connecting feature is received in the receptacle, and the first and second bodies are aligned.

In an embodiment, the first blade has a first leading point and a first trailing portion, wherein the second blade has a second leading point and a second trailing portion, wherein the first and second leading points diverge outward from the first body, wherein the first and second trailing portions converge toward the first body.

In another embodiment, the second arm is longer than the first arm.

In yet another embodiment, the protruding connection feature has prongs extending longitudinally from the first body.

In yet another embodiment, the second component rotates relative to the first component.

In yet another embodiment, the protruding connecting feature rotates within the receptacle.

In yet another aspect of the technology, a fusion device has a central portion with a sharpened biconcave leading edge, a blunt trailing end, a first lateral end and a second lateral end opposite the first lateral end; a first lateral blade transversely mounted to the first lateral end of the central portion; and a second lateral blade transversely mounted to the second lateral end of the central portion.

In an embodiment, the blunt trailing end is concave.

In another embodiment, the first lateral blade has serrations.

In yet another embodiment, the first lateral blade has a first exterior surface and a first interior surface opposite the first exterior surface, wherein the first exterior surface faces away from the central portion, wherein the first interior surface is sloped and intersects the first exterior surface at a first tip portion.

In yet another embodiment, the second lateral blade has a second exterior surface and a second interior surface opposite the second exterior surface, wherein the second exterior surface faces away from the central portion, wherein the second interior surface is sloped and intersects the second exterior surface at a second tip portion.

In yet another embodiment, the first and second tip portions diverge outwardly from the central portion.

BRIEF DESCRIPTION OF THE DRAWINGS

Various embodiments of the present disclosure will now be discussed with reference to the appended drawings. It will be appreciated that these drawings depict only typical examples of the present disclosure and are therefore not to be considered limiting of its scope.

DETAILED DESCRIPTION

While certain embodiments are shown and described in detail below by way of illustration only, it will be clear to the person skilled in the art upon reading and understanding this disclosure that changes, modifications, and variations may be made and remain within the scope of the technology described herein. Furthermore, while various features are grouped together in the embodiments for the purpose of streamlining the disclosure, it is appreciated that features from different embodiments may be combined to form additional embodiments which are all contemplated within the scope of the disclosed technology.

Not every feature of each embodiment is labeled in every figure in which that embodiment appears, in order to keep the figures clear. Similar reference numbers (for example, those that are identical except for the first numeral) may be used to indicate similar features in different embodiments.

Any of the devices described herein may be fabricated from metals, alloys, polymers, plastics, ceramics, glasses, composite materials, or combinations thereof, including but not limited to: PEEK (polyether ether ketone), commercially pure titanium, titanium alloys, ASTM F67, Nitinol, cobalt chrome, cobalt chrome alloys, stainless steel, UHMWPE (ultra-high molecular-weight polyethylene) and biodegradable materials, among others. Different materials may be used within a single part. The implants disclosed herein may also encompass a variety of surface treatments or additives to encourage bony attachment, including but not limited to: porous coatings, hydroxyapatite, tricalcium phosphate (TCP), anti-microbial additives, analgesics, anti-inflammatories, bone morphogenic proteins (BMPs), phorbol myristate acetate (PMA), bone growth promoting material, poly-L-lactide (PLLA), polyglycolide (PGA), tricalcium phosphate (TCP), demineralized bone, cancellous bone chips, etc. Any implant disclosed herein may include a radiographic marker for imaging purposes. Any implant disclosed herein may be colored, coded or otherwise marked to make it easier for the surgeon to identify the type and size of the implant.

Figure 1:
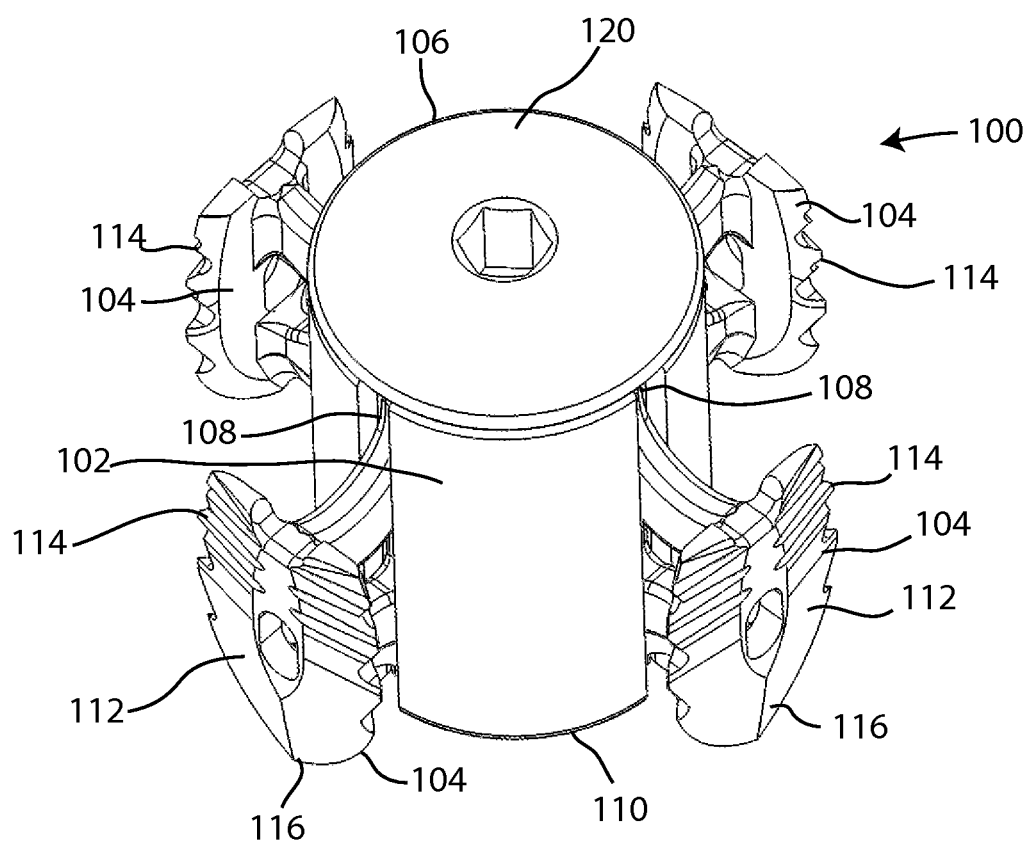
FIG. 1 is a front oblique view of a fusion device.
Figure 2:
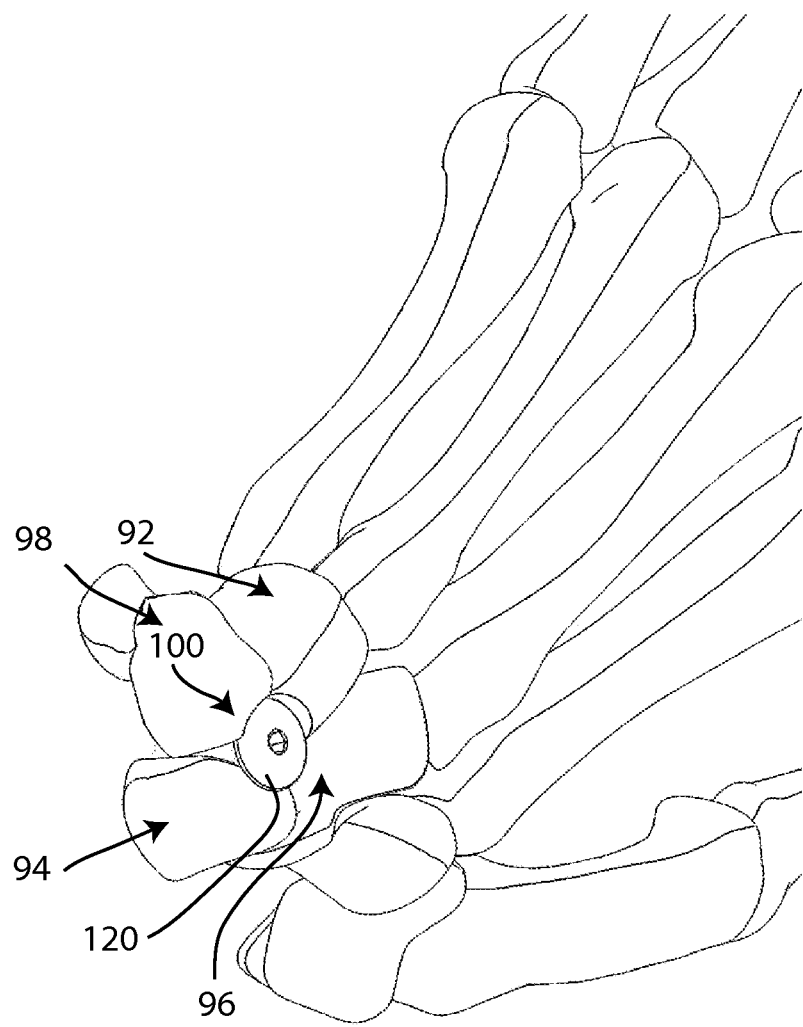
FIG. 2 is an oblique view of the fusion device of FIG. 1 implanted among carpal bones of a wrist.
Figure 3:
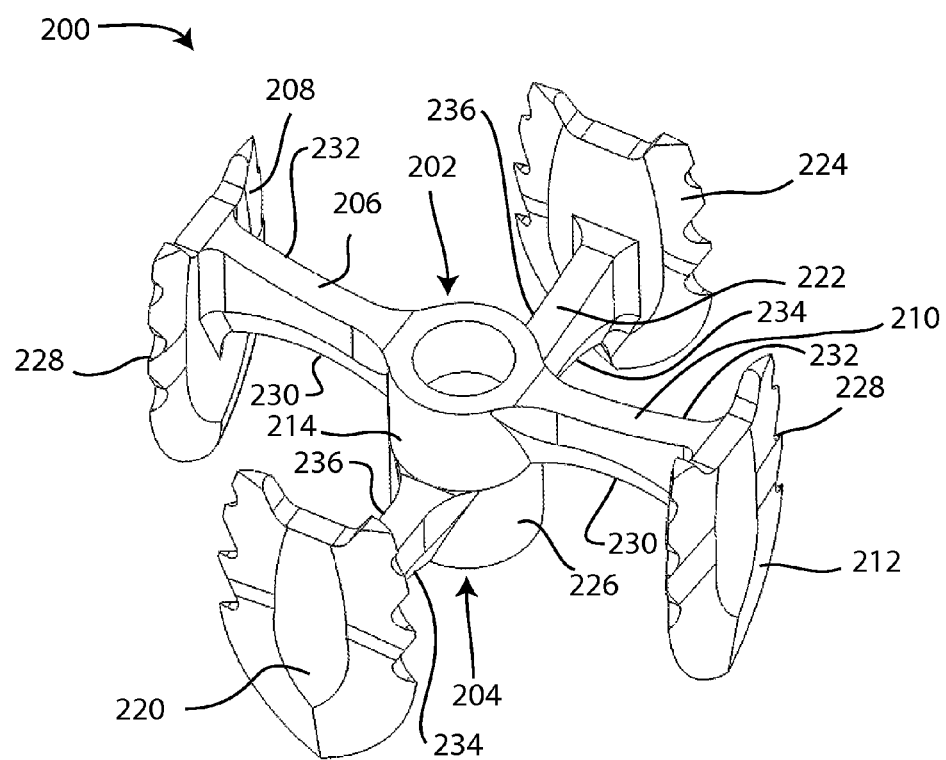
FIG. 3 is a front oblique view of another fusion device.

FIGS. 1-2 illustrate a fusion device that may be used to fuse a set of carpal bones, specifically the hamate, lunate, capitate and triquetrum. The fusion device includes a body and a plurality of anchors that extend radially from the body.

As seen best in FIG. 1, fusion device 100 includes a body 102, which may be cylindrical and may include a proximal first end 106 and a distal second end 110. The body 102 may also be polygonal, oval, elliptical, asymmetric, or irregular in cross section instead of circular, as for a cylindrical body. The body 102 may be smooth, or may be externally textured, for example, threaded, ridged, or studded. The body 102 may include a plurality of undercut slots 108, channels, or grooves along the surface that may extend between the first end 106 and the second end 110. The slots, channels, or grooves may act as connecting features for one or more bone anchors. Dovetail, T, or cylindrical protrusions on the anchors may engage correspondingly shaped slots 108, channels, or grooves in the body. In the example of FIGS. 1-2, the body 102 includes four grooves 108 and four anchors 104. The body 102 may be centrally, eccentrically, symmetrically, or asymmetrically located among the anchors 104. The grooves 108 may remain stationary along the surface of the body 102, or may be allowed to rotate around the axis of the body 102 to be better placed for blade anchor insertion. For example, the grooves 108 may be allowed to rotate about a central longitudinal axis of the body 102.

The anchors 104 may include an outward face 112 that includes blades 114, fins, barbs, teeth or other features to drive the fusion device 100 into the carpal bones. The blade anchors 104 may include a tapered portion 116. The anchors 104 may share some or all of the characteristics of the bone anchors disclosed in U.S. patent application Ser. No. 12/640,892, which is incorporated herein in its entirety.

When fusion device 100 is assembled, the blade anchors 104 may be at least partially contained within the grooves 108 and may extend radially outward from the body 102. The blade anchors 104 may be axially moveable along the grooves 108 to be driven into the carpal bones. The blade anchors 104 may be variably offset from the body 102 to accommodate various patient anatomies. Additionally, to accommodate various patient anatomies, multiple bodies 102 may be placed adjacent to one another, creating, for example, a figure-eight configuration. The multiple bodies may be formed integrally with each other, or may be modularly connectable by fitting a projection on a second body into a groove on a first body.

The end 106 of body 102 may also include a proximal threaded portion (not shown) to connect to a threaded cap 120 that may be placed onto the first end 106 body 102 after blade anchor insertion. The cap 120 may be axially aligned to the body 102 to lock the blade anchors 104 in place as well as provide a smooth articulation with dorsal tendons. The cap 120 may include generous edge breaks to soften exterior edges with fillets or chamfers. The cap 120 may also be polished to further smooth surfaces which face or contact soft tissues.

FIG. 2 provides a proximal view of fusion device 100 embedded into the wrist joints to fuse the four carpal bones: hamate 92, lunate 94, capitate 96, and triquetrum 98. The device proximal threaded cap 120 can be seen to be nearly continuous with the surface of the bones.

Fusion device 100 may also include additional cut-outs or fenestrations (not shown) for osseus ongrowth/ingrowth means. The fusion device 100 may be filled with biologics for osteoinduction and osteoconduction, the biologics accessible to the host tissues through the cut-outs or fenestrations. The fenestrations may be located in the body, for instance between the grooves 108, or in the end 110. Fenestrations may also be located in the cap 120 in some examples.

FIGS. 3-7 illustrate another example of a fusion device that includes a plurality of blade anchors and a minimalistic body. The blade anchors may provide compression across a fusion or fracture line in any application where a typical bone staple could be used, such as in small bone osteosynthesis or sternal closure.

Fusion device 200 may include at least two components, or staples, that are connected via a central mechanism, allowing fragments to be compressed towards a single point or axis. Fusion device 200 includes a first component 202, and a second component 204.

Figure 4:
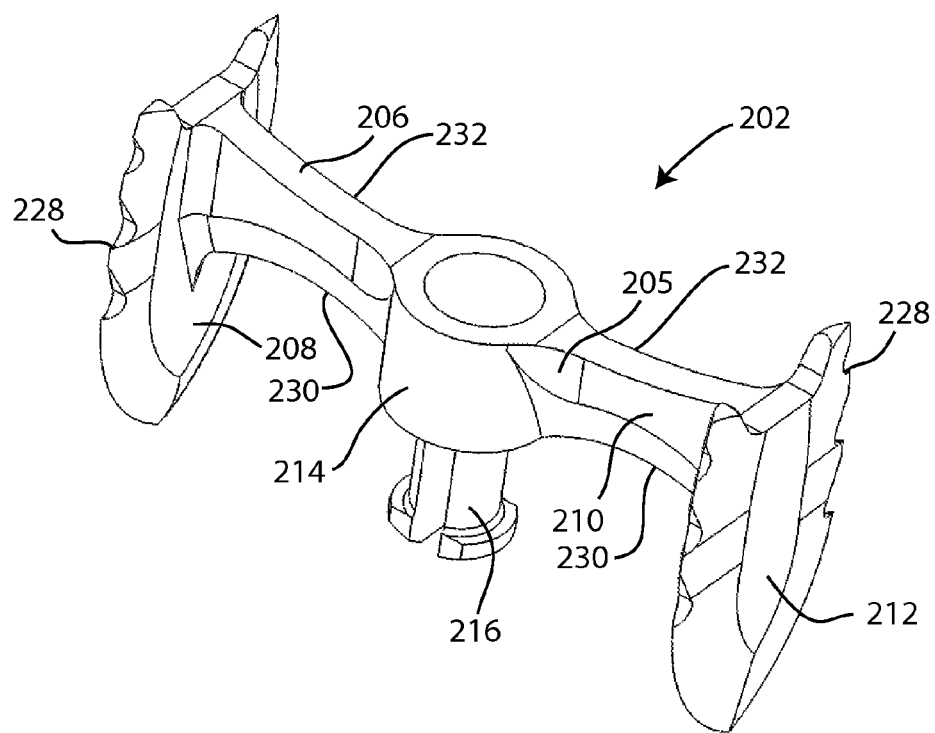
FIG. 4 is a front oblique view of a component of the fusion device of FIG. 3.
Figure 5:
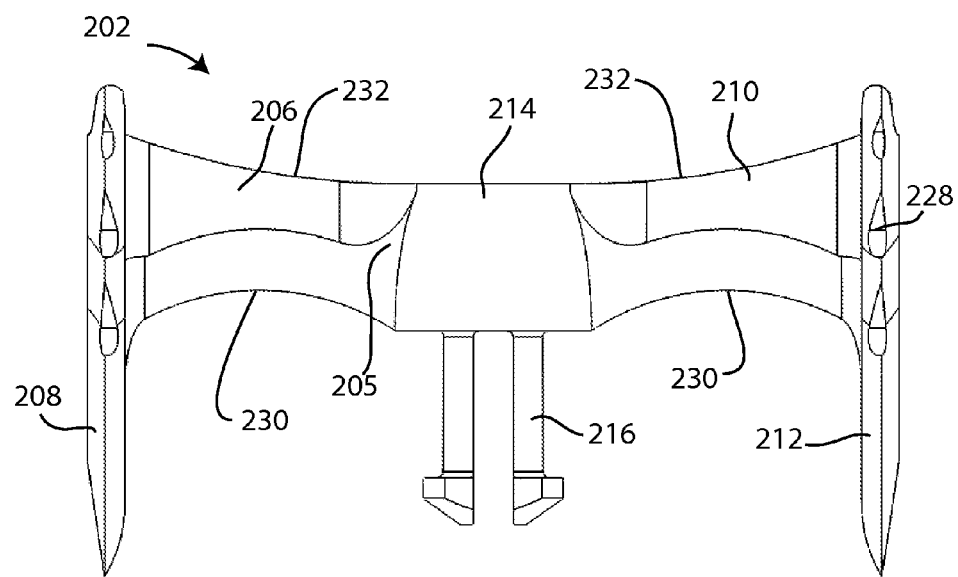
FIG. 5 is a front view of the component of FIG. 4.

Referring to FIGS. 4-5, the first component 202 includes a body 205, a first arm 206 that terminates in a first blade 208, and a second arm 210 that terminates in a second blade 212, the second arm 210 opposite the first arm 206.

The first blade 208 may be oriented perpendicular to the length of the first arm 206 in two planes and the second blade 212 may be oriented perpendicular to the length of the second arm 210 in three planes, and the arms 206, 210 may be mutually parallel and collinear. This orthogonal arrangement is one example of the contemplated range of all angles between the arms and blades. Other examples include blades whose tips diverge or converge, a blade forming an acute angle with an arm in one or more planes, or arms forming an included obtuse or acute angle between them in one or more planes. The length of the first arm 206 and the second arm 210 may be variable to accommodate different patient anatomies and different applications. For example, the first and second arms 206, 210 may have equal or unequal lengths. A set of first components having a range of arm lengths may be provided. The first component also includes a central portion 214, located between the first arm 206 and the second arm 210. The first and second arms 206, 210 may be said to extend radially from the central portion 214. The first and second arms 206, 210 may have concave leading edges 230 and blunt trailing ends 232. Together, the first and second arms 206, 210 may be said to provide a biconcave leading edge. The central portion 214 may include a connecting feature 216 that extends outward from the body 203. The connecting feature 216 may be a snap hook to prevent axial separation, a taper connection to prevent axial rotation and separation with a friction fit, a connecting feature that allows translation along the length of the first component 202, or a cap or clip to maintain the connection. In the illustrated example, the connecting feature 216 includes prongs which extend longitudinally from the body 203. Each prong may include a lip extending radially from the prongs, wherein each lip may provide a snap fit or other reversible fixation with the second component 204. The first component shown in FIGS. 4-5 may be described as a male staple.

Figure 6:
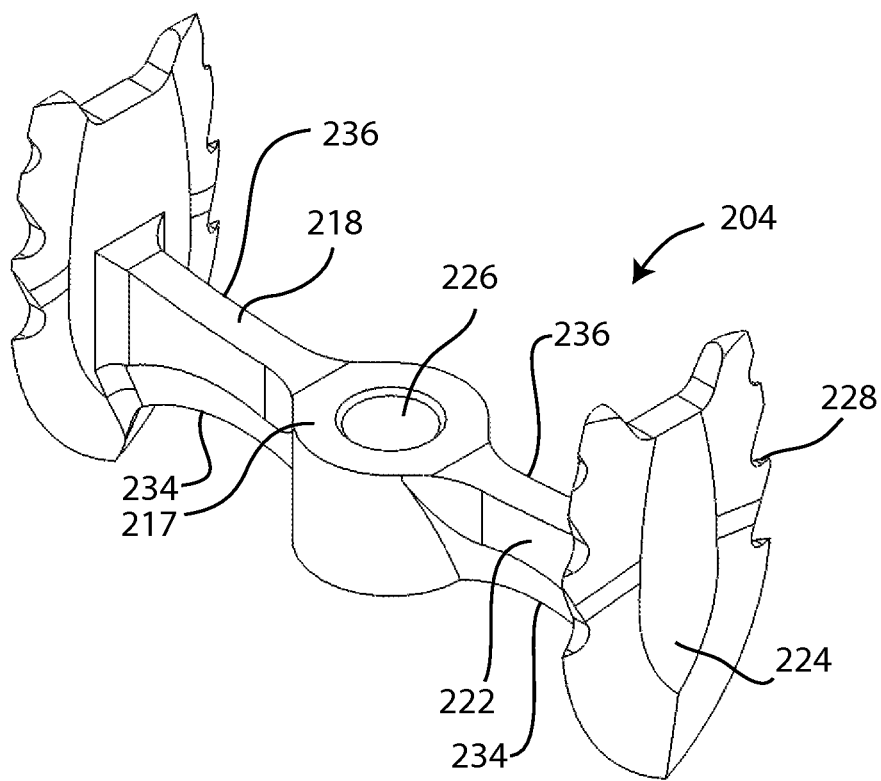
FIG. 6 is a front oblique view of another component of the fusion device of FIG. 3.
Figure 7:
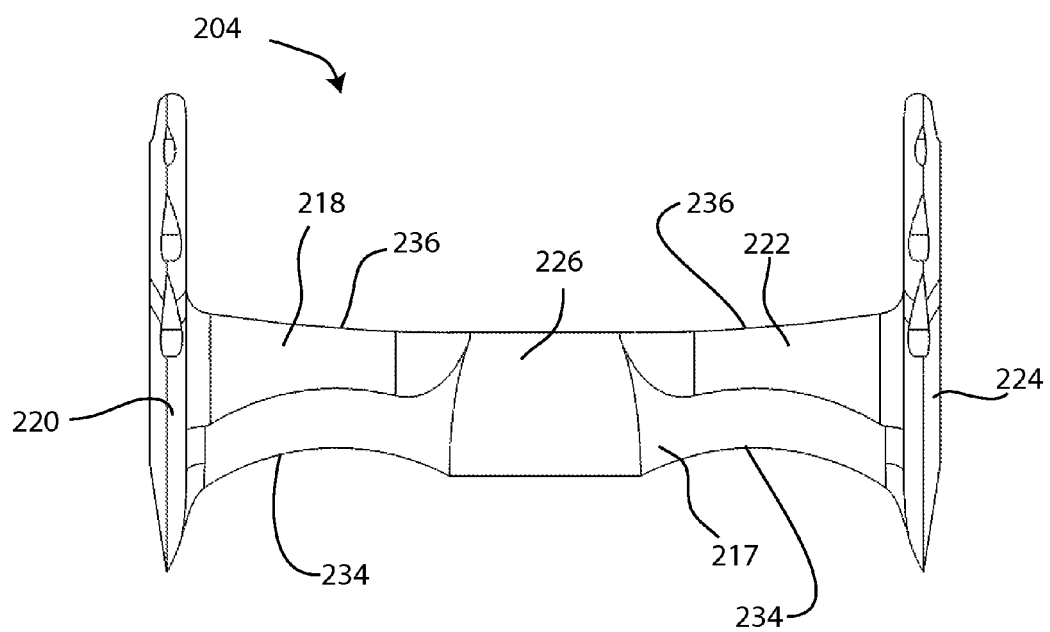
FIG. 7 is a front view of the component of FIG. 6.

Referring to FIGS. 6-7, the second component 204 also includes a body 217, a first arm 218 that terminates in a third blade 220, and a second arm 222 that terminates in a fourth blade 224, the second arm 222 opposite the first arm 218. While an orthogonal arrangement is shown, all other angular relationships between at least the arms and blades are contemplated. The second component 204 also includes a central portion 226, located between the first arm 218 and the second arm 222, which may be an aperture, receptacle, or socket shaped to receive the connecting feature 216 of the male connection staple. The first and second arms 218, 222 may be said to extend radially from the central portion 226. The first and second arms 218, 222 may have concave leading edges 234 and blunt trailing ends 236. Together, the first and second arms 206, 210 may be said to provide a biconcave leading edge. The second component 204 shown in FIGS. 6-7 may be described as a female staple.

When the connecting feature 216 engages the central portion 226 of the female connection staple 204, the male connection staple 202 and the female connection staple 204 become joined or coupled together such that the first blade 210, the second blade 212, the third blade 220 and the fourth blade 222 may extend outward from the connected, aligned central portions 214, 226 to engage the carpal bones such that the staples 202, 204 may become axially fixed, rotationally fixed, or both.

Each of the blades 208, 212, 220, 224 may be angled or contain at least one angled surface to provide enhanced compression between opposing bones. For example, a blade may be angled so that a tapered leading point of the blade is farther from the corresponding body than a trailing rear portion of the blade, so that as the blade penetrates the bone, the bone is urged toward the body. In an arrangement where every blade is so angled, each blade may urge a separate bone or bone fragment toward the body. Each of the blades 208, 212, 220, 224 may also include additional fixation features 228 such as teeth, serrations, or barbs to enhance their interaction with the bones, such as to inhibit backward migration of the blade out of the bone after implantation. The connection between the female connection staple 204 and the male connection staple 202 may not constrain all degrees of freedom, as the carpal bones may provide sufficient rotational constraint once the fusion device is implanted.

Figure 8:
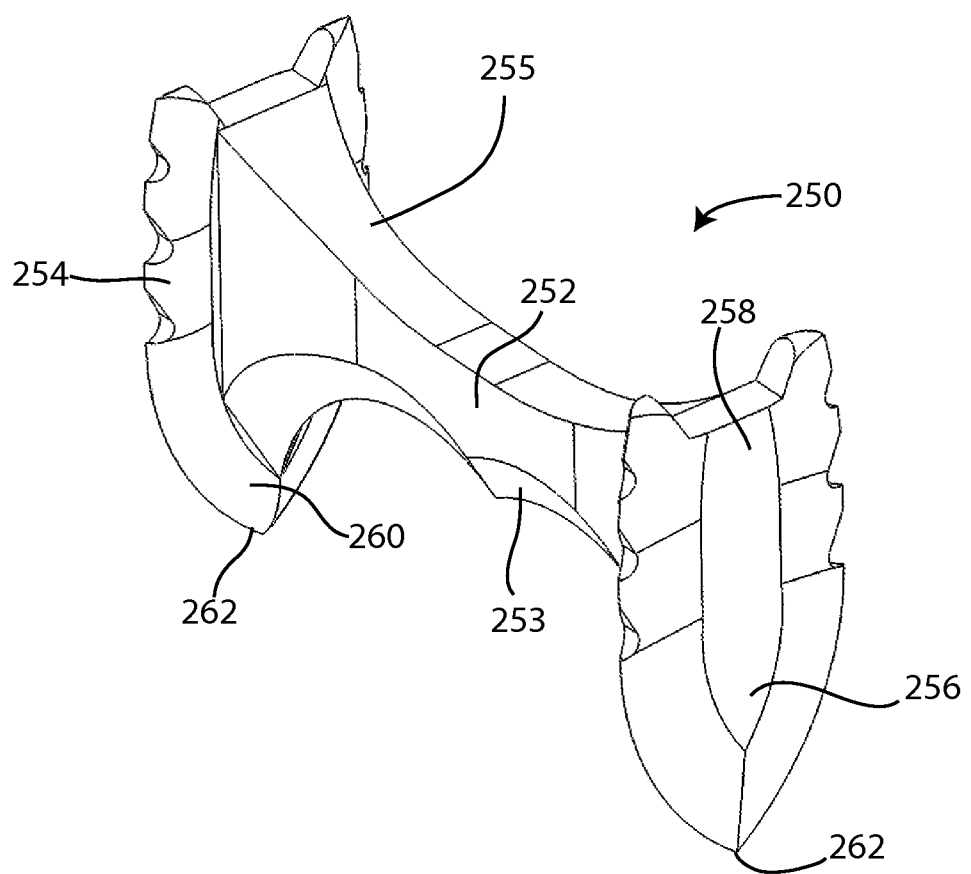
FIG. 8 is a front oblique view of yet another fusion device.
Figure 9:
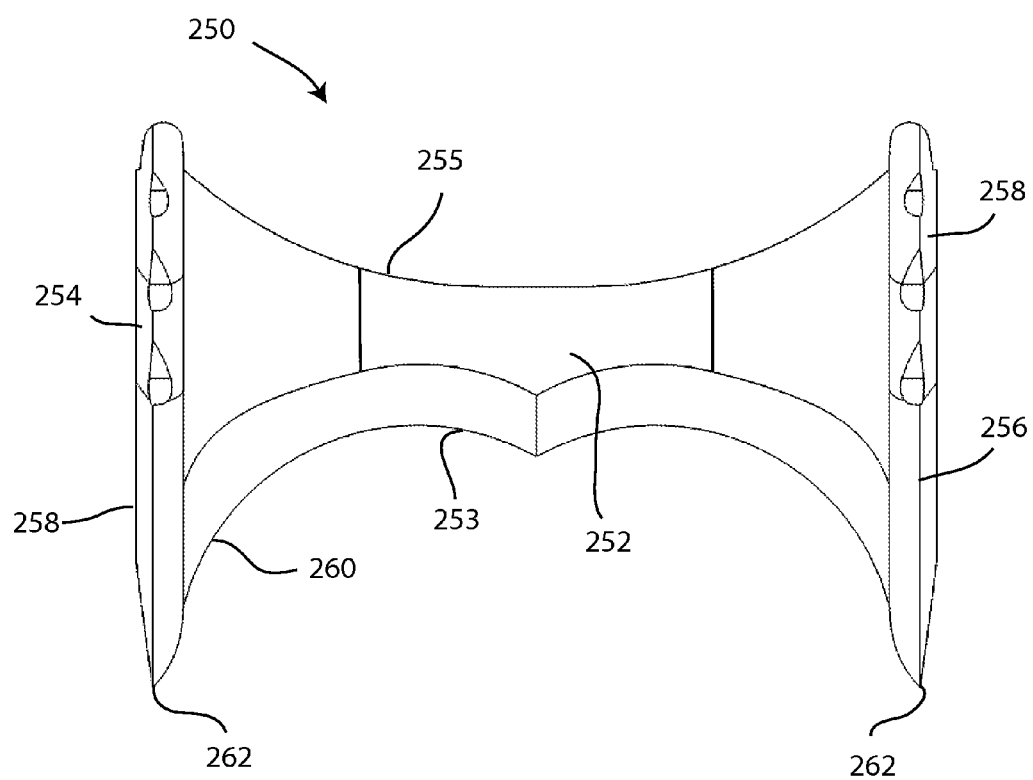
FIG. 9 is a front view of the fusion device of FIG. 8.

FIGS. 8 and 9 illustrate a fusion device 250 with at least two blades 254, 256, and no connecting feature. Fusion device, or staple 250 includes a central portion 252 and two lateral blades 254, 256. The central portion 252 may have a sharpened biconcave leading edge 253 and a blunt trailing end 255. The blades may have features similar to those previously described, and may contain an exterior surface 258 that faces away from the central portion and an interior surface 260 opposite the exterior surface 258. The interior surface 260 may be sloped and may intersect that exterior surface 258 at a tip portion 262. The orthogonal arrangement shown is one example of the range of all angular relationships which are contemplated in the scope of this disclosure.

In operation, a first compression staple may be placed proximal to and crossing a second compression staple. The slope of the interior surfaces 260 may create a wedge effect to create compression and achieve the desired orientation for fusion applications.

It should be understood that the present components, systems, kits, apparatuses, and methods are not intended to be limited to the particular forms disclosed. Rather, they are intended to include all modifications, equivalents, and alternatives falling within the scope of the claims. They are further intended to include embodiments which may be formed by combining features from the disclosed embodiments, and variants thereof.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, a blade configuration from one or more fixation device examples may be found on the other fixation device examples disclosed herein. Similarly, manufacturing, assembly or implantation methods described for one fixation device or component may be used in the manufacture, assembly or implantation of the other fixation devices or components disclosed herein. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A fusion device comprising:
a first component comprising a first body, a first arm, a first blade, and a protruding connecting feature, wherein the first arm comprises a concave first leading edge and a blunt first trailing end, wherein the first arm extends outward from the first body and terminates in the first blade, wherein the first blade extends transverse to the first arm, wherein the first blade comprises a first sharp tapered point and a first trailing portion opposite the first sharp tapered point, wherein the protruding connecting feature protrudes from the first body; and a second component comprising a second body, a second arm, a second blade, and a receptacle, wherein the second arm comprises a concave second leading edge and a blunt second trailing end, wherein the second arm extends outward from the second body and terminates in the second blade, wherein the second blade extends transverse to the second arm, wherein the second blade comprises a second sharp tapered point and a second trailing portion opposite the second sharp tapered point, wherein the receptacle is recessed within the second body;
wherein when the first and second components are coupled together, the protruding connecting feature is received in the receptacle, the first and second bodies are aligned, the first leading edge, the first tapered point, the second leading edge, and the second tapered point all face the same way, the first and second tapered points diverge outward from the first body, and the first and second trailing portions converge toward the first body.

2. The device of claim 1, wherein the second arm is longer than the first arm.

3. The device of claim 1, wherein the protruding connection feature comprises prongs extending longitudinally from the first body.

4. The device of claim 1, wherein the second component rotates relative to the first component.

5. The device of claim 4, wherein the protruding connecting feature rotates within the receptacle.

6. A fusion device comprising:
a first component comprising a first body, a first arm, a first blade, and a protruding connecting feature, wherein the first arm comprises a concave first leading edge and a blunt first trailing end, wherein the first arm extends outward from the first body and terminates in the first blade, wherein the first blade extends transverse to the first arm, wherein the first blade comprises a first sharp tapered point and a first trailing portion opposite the first sharp tapered point, wherein the protruding connecting feature protrudes from the first body; and a second component comprising a second body, a second arm, a second blade, and a receptacle, wherein the second arm comprises a concave second leading edge and a blunt second trailing end, wherein the second arm extends outward from the second body and terminates in the second blade, wherein the second blade extends transverse to the second arm, wherein the second blade comprises a second sharp tapered point and a second trailing portion opposite the second sharp tapered point, wherein the receptacle is recessed within the second body;
wherein when the first and second components are coupled together, the protruding connecting feature is received in the receptacle, and the first and second bodies are aligned.

7. The device of claim 6, wherein the first blade comprises a first tapered point and a first trailing portion opposite the first tapered point, wherein the second blade comprises a second tapered point and a second trailing portion opposite the second tapered point, wherein when the first and second components are coupled together, the first leading edge, the first sharp tapered point, the second leading edge, and the second sharp tapered point all face the same way, the first and second sharp tapered points diverge outward from the first body, and the first and second trailing portions converge toward the first body.

8. The device of claim 6, wherein the second arm is longer than the first arm.

9. The device of claim 6, wherein the protruding connection feature comprises prongs extending longitudinally from the first body.

10. The device of claim 6, wherein the second component rotates relative to the first component.

11. The device of claim 10, wherein the protruding connecting feature rotates within the receptacle.

* * * * *